United States Patent [19]
Atwood et al.

[11] 3,963,909
[45] June 15, 1976

[54] METHOD AND APPARATUS FOR COMPUTATION IN A KINETIC ANALYZER

[75] Inventors: John G. Atwood, Redding; Peter H. Heinz, Trumbull, both of Conn.

[73] Assignee: The Perkin-Elmer Corporation, Norwalk, Conn.

[22] Filed: Aug. 22, 1974

[21] Appl. No.: 499,616

[52] U.S. Cl. .......................... 235/151.35; 235/183; 356/96; 23/230 R
[51] Int. Cl.² ................... G06G 7/18; G01N 21/22; G01J 3/42
[58] Field of Search ............. 235/151.35, 151.3, 183, 235/92 E, 92 CA; 356/213, 215, 88, 96, 204, 205; 23/230 R, 253 R

[56] References Cited
UNITED STATES PATENTS

| | | | |
|---|---|---|---|
| 3,489,885 | 1/1970 | Kintner | 235/183 X |
| 3,624,649 | 11/1971 | Ranieri | 235/92 EV X |
| 3,646,331 | 2/1972 | Lord | 235/151.3 |
| 3,664,744 | 5/1972 | Liston | 356/88 |
| 3,701,601 | 10/1972 | Plumpe, Jr. et al. | 356/96 |
| 3,764,268 | 10/1973 | Kosowsky et al. | 23/253 R |
| 3,813,532 | 5/1974 | Sato et al. | 235/183 |
| 3,847,486 | 11/1974 | McCabe | 356/96 X |

*Primary Examiner*—Edward J. Wise
*Attorney, Agent, or Firm*—Sal A. Giarratana; Francis L. Masselle; John M. O'Meara

[57] ABSTRACT

The nominally linear reaction rate and the curvature thereof are computed over an observation period by integrating the absorbance signal in opposite directions during portions of the observation period.

34 Claims, 6 Drawing Figures

METHOD AND APPARATUS FOR COMPUTATION IN A KINETIC ANALYZER

BACKGROUND OF THE INVENTION

This invention relates to photometric analysis in general and more particularly to an improved method and apparatus for computation of rates in a photometric analyzer.

In application Ser. No. 499,602 filed Aug. 22, 1974, now abandoned, and assigned to the same assignee as the present invention a completely automated kinetic analyzer is disclosed. This application has now been abandoned and a continuation application Ser. No. 594,951 filed July 10, 1975 has been filed on the subject matter thereof. One of the primary problems in constructing such an analyzer is in providing a method of computing rates of absorbance to provide final outputs in a manner which is accurate and reliable. In addition to making an accurate measurement of rate, means must also be provided to insure that the linearity of the output change from a photometer or the like is within pre-established limits. If such is not done erroneous outputs can result.

Typically in the prior art such measurements have been made by measuring at two points in time and the difference between the two measurement values used as an indication of rate. Since the outputs which are being measured in such a device are subject to noise variations this prior art measurement method can result in large errors. It is possible for example for the one measurement to be taken at a peak and the other measurement to be taken at a valley of the super-impressed noise thereby resulting in an output much in error. Furthermore in prior art apparatus in making a check of linearity and doing what is referred to in the art as a curvature check, pre-established curvature limits have normally been set. These curvature limits are used no matter what the rate being measured turns out to be. Clearly the tolerance for curvature will depend on the rate. That is to say that a curvature which might be excessive for a low rate could be perfectly acceptable for a high rate since such curvature would cause the final result to be only slightly in error. However the allowable curvature for the high rate if applied to a low rate would result in completely unacceptable outputs. Because of this, in the prior art apparatus, the curvature limit has been set on the low side. Consequently many rate measurements which are actually valid must be thrown out because of a rejection based on excessive curvature. This of course raises the time required and the expense of carrying out tests of this nature.

Although the prior art apparatus did reject rate measurements having excessive curvature and possibly suffering from other deficiencies they gave the operator no clear indication of what caused the rejection. A clue as to what caused a bad reaction many times can be helpful in determining whether the apparatus is operating incorrectly or whether some other problem exist.

In view of these various deficiencies the need for an improved computation method and apparatus became evident to the inventors herein.

SUMMARY OF THE INVENTION

The computation method of the present invention solves these various problems associated with prior art computing apparatus.

The kinetic reaction rate and curvature measurement and the error checking system of the present invention provides features not found in the prior art. The absorption of the reaction mixture is continuously observed over a measuring time and converted to a analog voltage linearly related to absorption. This signal is then converted to a pulse frequency modulated signal having a frequency linearly related to absorption. The pulse frequency modulated signal is integrated by counting pulses in one direction with a reversible counting register for the first half of the measuring time and then reversing the direction of counting for the second half of the measuring time. As a result, the final net count is proportional to the average rate of change of the absorption signal over the measuring period. Measurement in this way means that the final output is a measure of the change over the full measuring period. Clearly, this method of measurement is much superior to methods taking a reading at the beginning and end of the period and subtracting the results. With such methods which were generally used in the prior art, it is possible to obtain greatly erroneous results because of the fact that random variations in the absorbance can occur at various points in the measuring cycle due to solid material and so on in the sample. Also, the present invention provides that while the rate is being computed, an accumulation of the same pulse train in a second reversible counting register occurs with counts being accumulated in one direction for the first quarter of the measuring time, the direction of counting reversed to accumulate the counts for the second and third quarters of the measuring time in the opposite direction, and the direction of counting again reversed to accumulate the counts for the fourth quarter of the measuring time in the first direction, as a result the final net count is proportional to the curvature of the rate or a measure of its linearity. The count stored in the curvature register is compared with that in the rate register and if it exceeds a certain percentage of the rate count, an error signal is printed out. Specific means for doing this are disclosed in detail. Computation in this manner has two beneficial effects. In the first place, since the rate and curvature computations are done simultaneously, no time is wasted. Furthermore, making the decision as to whether the rate observed is within limits based on a percentage of the rate is superior to prior art methods where if an arbitrary curvature value was exceeded, the rate measurement was considered bad regardless of its magnitude. In addition, an indication is given as to the sign of the curvature where an excessive error exists. This gives the operator a clue as to what occurred during the measurement which caused excessive curvature, e.g., an accelerating rate or use up of reagent.

DETAILED DESCRIPTION OF THE PREFERRED EMBODIMENT

The system disclosed herein has as its purpose the computations necessary to kinetic analysis and particularly the computation of reaction rate and its curvature from the outputs of photodetectors and 1 or 2 preamplifiers which are proportional to parameters such as absorbance. In addition to application Ser. No. 499,602 mentioned previously, typical apparatus for providing an absorbance signal to the system of the present invention is disclosed in application Ser. Nos. 499,617 and 499,855 both filed on Aug. 22, 1974 and assigned to the same assignee as the present invention.

Before describing how the computations are accomplished, the nature and significance thereof will be discussed briefly. In kinetic analysis, what occurs after the two reagents are mixed together with the sample, the absorption thereof changes proportionally with reaction rate. After a startup period, this change should occur linearly until the reagent is used up, at which time the change will taper off. The change may be an upward change or a downward change depending on the particular test being run. That is, the absorption may increase or decrease during the reaction. The measure of the serum activity is determined by the reaction rate but to have an accurate indication thereof, it is necessary to insure that the rate is being measured while the reaction is. To insure this, a curvature measurement must also be made. As will be explained in more detail below, the rate and curvature are measured simultaneously by the apparatus of the present invention. This is in contrast to prior art apparatus which first did a curvature check and then measured rate. A disadvantage of this prior method was that a portion of the measurement time had to be used up in making the curvature measurement leaving only the remaining portion for the rate measurement. A second disadvantage was that an allowable curvature needed to be pre-established before knowing the rate produced by any sample. The present invention on the other hand establishes allowable curvature as a function of the rate and thus can test samples which would otherwise be rejected by prior art apparatus. In particular it allows a sample with a higher rate to have higher curvature so that maximum allowable error due to curvature is a fixed percentage. More importantly, it uses the full measurement time available. It does this is a number of ways as will become more clear below.

Figure 1:
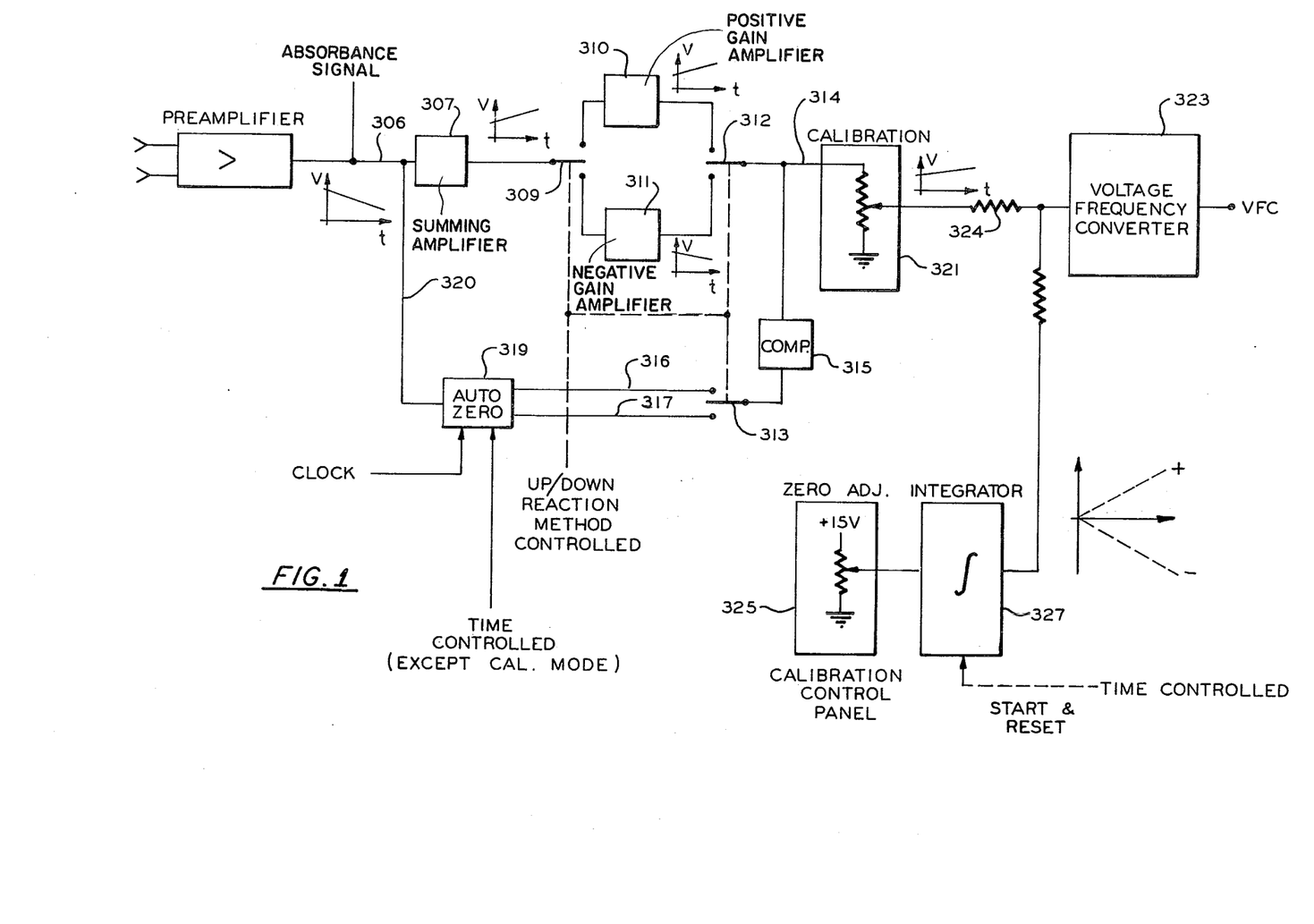
FIG. 1 is a block-schematic diagram illustrating the auto zeroing apparatus by which the absorbance signal is converted to frequency within the scope of the present invention.
Figure 1A:
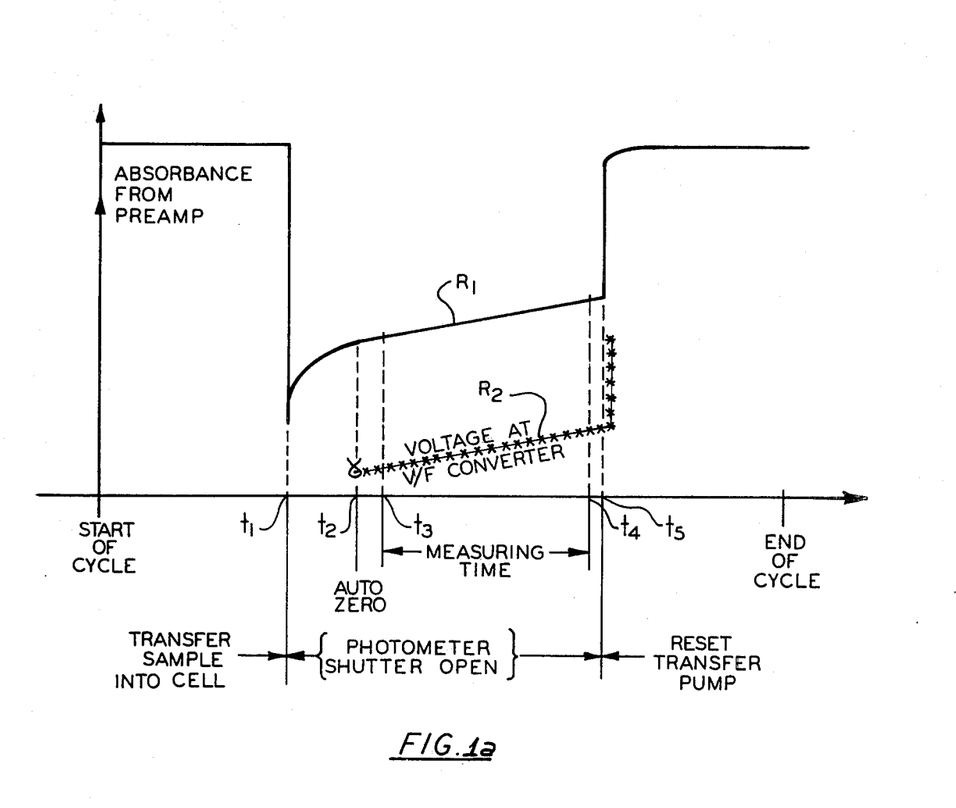
FIG. 1a is a timing diagram illustrating operation of a typical photometer system during a measurement cycle.

An understanding of signal conditioning and generation for kinetic analysis can best be obtained through an examination of FIGS. 1 and 1a. FIG. 1a illustrates the programmed events of each measuring cycle. As indicated in the description of the above referenced applications, a shutter in a photometer remains closed until the sample is in a cell. As shown by FIG. 1a, the absorbance signal from the pre-amplifier of FIG. 1 at a maximum with the shutter closed. The shutter is opened at a time $t1$. Nothing is done immediately thereafter in order to allow everything to stabilize for a short period. At time $t2$ an auto zero cycle stage is started and curve R1 shows the manner in which the pre-amplifier output would change without auto zero. The curve R2 shows the effect of auto zero which brings the level of the absorbance signal down near zero so that the higher gain may be utilized during the measuring time stage. After the end of auto zero, at time $t3$, the measuring time begins and continues until time $t4$. Thereafter, at time $t\,5$ the shutter is closed and the transfer pump goes through its reset stage.

Referring now to FIG. 1, the absorbance signal on line 306 is provided to a summing amplifier 307 with output therefrom being connected through a first switch 309 to either an amplifier 310 with a gain of +2 or an amplifier 311 with a gain of −2. This is only a symbolic amplifier change. Actually the amplifiers 310 and 311 constitute one amplifier used in the described manner, Since the voltage to frequency converter at the output of FIG. 1 can only operate at one polarity, it is essential that only positive signals be provided thereto. Thus, if the sample being tested is one having a decreasing reaction, then inversion is necessary. A second switch 312 synchronized with switch 309 is provided at the output of the amplifiers 310 and 311. These two switches can, of course, be transistor or FET switches rather than mechanical switches. A third switch synchronized with switches 309 and 312 and designated 313 is also provided. This switch can be logic gates and couples the output of a comparator 315 which has as its input the signal on line 314 from one of the amplifiers 310 or 311. Comparator 315 is preset to a threshold level close to zero, e.g. + 0.7 V., with output therefrom being provided on one of the lines 316 or 317 to an auto zero logic circuit 319. The output of the auto zero logic circuit 319 is provided as a second input to the summing amplifier 307. A counter, a digital to analog converter and appropriate gating are arranged in the auto zero circuit 319 to provide an output on line 320 which drives the output of amplifier 307 toward the +0.7V threshold of the comparator 315. This circuit and the operation thereof is well known in the art, such as from U.S. Pat. No. 3,800,236 issued on Mar. 26, 1974. In this patent, counter 22 is enabled to count clock pulses from generator 30 through an AND gate 20 until the threshold of logic circuit 32 (a comparator) is exceeded at which time the count is stopped. Output from counter 22 is applied to the digital to analog 24 from which output is fed back negatively or subtracted from the input 16. Clearly, other types of auto zeroing can be used, such as those disclosed in U.S. Pat. Nos. 3,579,105 issued May 18, 1971; 3,634,770 issued Jan. 11, 1972; 3,754,232 issued Aug. 21, 1973; and 3,824,481 issued July 16, 1974. It will be recognized by those skilled in the art that what is being carried out is a closed loop integration and that in place of a clock and counter an analog integrator or motor integrator may also be used.

The output which is now near zero (+0.7V) is provided through a calibration potentiometer 321 and an input resistor 324 to the input of a voltage frequency converter 323. Although not shown, separate calibration potentiometers are provided for each wave length and in conjunction with the test selection will be switched into the circuit in conventional fashion using relays or semiconductor switches. Because a small slope can occur, i.e., an apparent change in absorption, which is not the result of the chemical reaction due to the sample being measured, compensation to offset this unwanted slope is also provided. Thus, there is included a zero adjust potentiometer 325 which is an input to an analog integrator 327. The integrator output is summed at the input to the voltage to frequency converter 323 with the signal from the calibration potentiometer 321. It is of course selected to be in a direction opposite to the unwanted slope. The integrator is started and reset by appropriate outputs from a timer. The voltage to frequency converter will convert the analog signal present at its input to an ouput whose frequency is proportional to the analog magnitude in well known fashion. A typical voltage to frequency converter which may be used for this purpose is type 1700-5044-00 from Anadax Instruments Inc.

Figure 2:
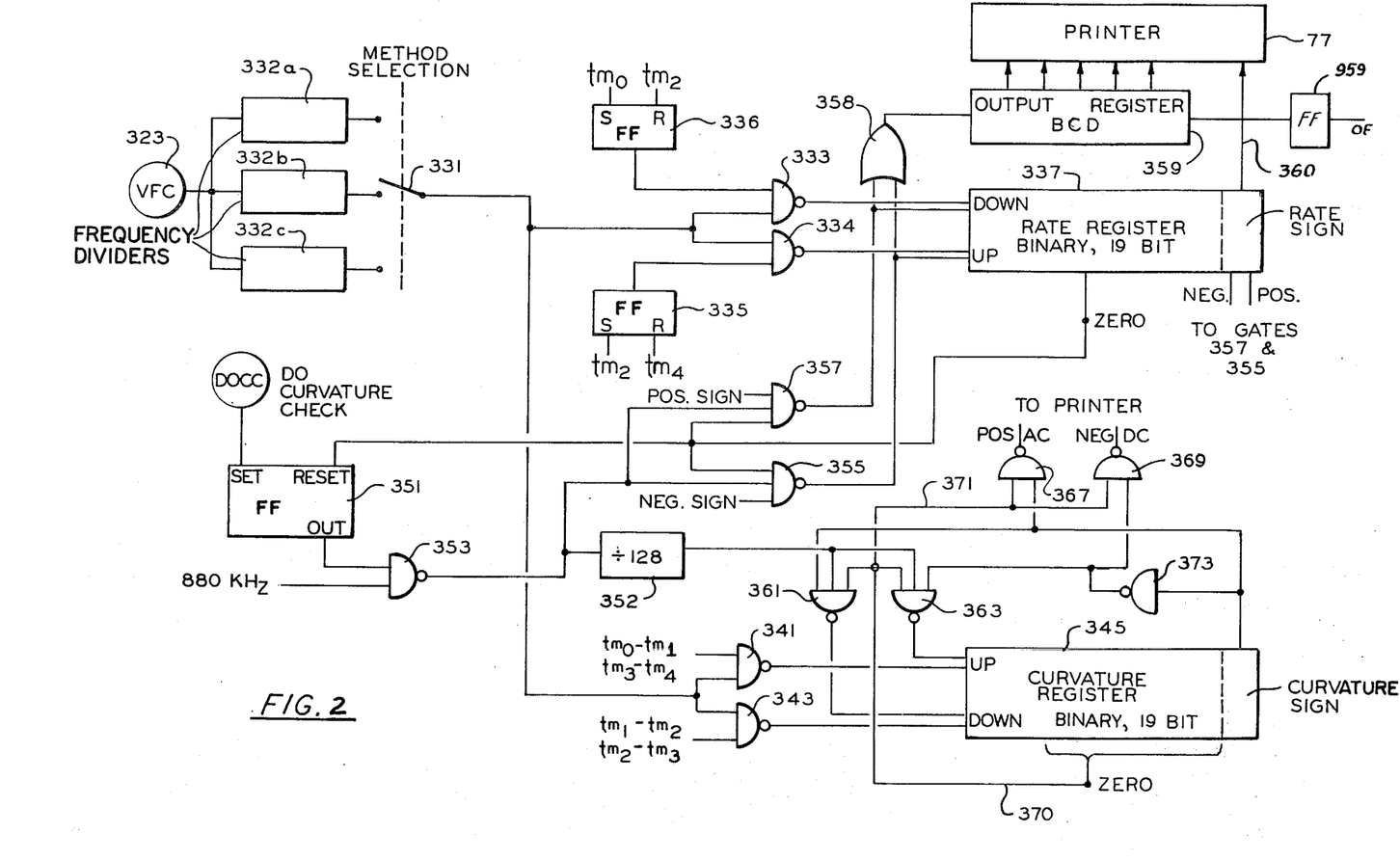
FIG. 2 is a logic diagram illustrating the manner by which reaction rate and curvature thereof is calculated from the frequency output of FIG. 1 in accordance with the present invention.
Figure 3:
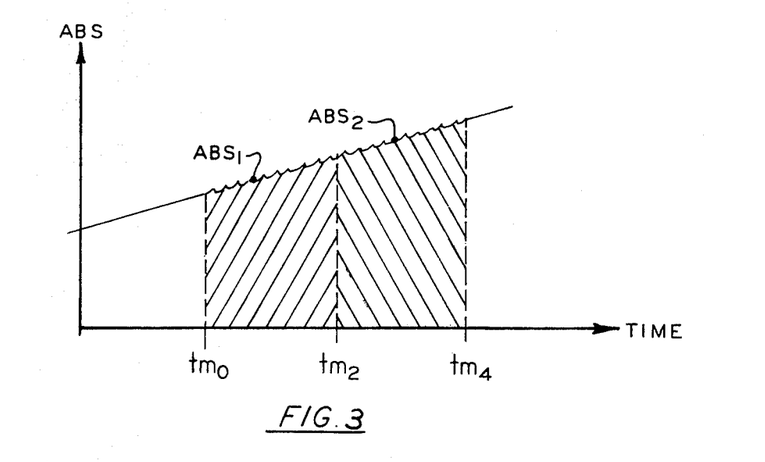
FIGS. 3 and 3a are diagrams helpful in understanding the apparatus of FIG. 2.

FIG. 2 illustrates the manner in which rate and curvature are calculated. FIG. 3 is a curve illustrating the manner in which the absorbance signal changes during the measurement period. As noted above, it is the rate or the change of absorption which is to be measured. The output of the voltage to frequency converter 323 is provided to three dividers. The dividers designated 332$a$ and 332$b$ and 332$c$ divide the frequency by predetermined factors depending on the test selected. The divider 332$a$ is associated with the wave length of 340 nm and the divider 332$b$ with the wave length of 404 nm. The final divider 332$c$ is used in conjunction with the auxiliary test and may be preset to divide by a number N/10,000. The output of one of these dividers, depending on which test is selected as described in the aforementioned pending continuation application Ser. No. 594,951 filed July 10, 1975, is provided to a pair of gates 333 and 334 through a switch 331, which can be made up of gates. These gates 333 and 334 are enabled respectively by signals from flipflops 335 and 336. The flipflops are set and reset by outputs from the timer. Thus, at the time $t_{m0}$ (See FIG. 3) flipflop 336 is set to enable the gate 333. Pulse output from the gate 333 is provided as a down input to a rate register 337 comprising a binary up-down counter. As long as the gate 333 is enabled, the counter counts down. With reference to FIG. 3, it counts down for the period between $t_{m0}$ and $t_{m2}$. This corresponds to one-half the measurement period. It will be recognized that such counting results in an integrating and averaging effect to the absorbance signal which, as illustrated, is not flat but contains noise. The count in the counter at the end of the first half of the measurement period at time $t_{m2}$ will be proportional to the average absorbance value over that period (ABS 1 indicated on FIG. 3) with much of the noise cancelled therefrom due to the integrating effect. At this point, flipflop 336 is reset and flipflop 335 set to enable gate 334 from which pulse output is provided as an up input to rate register 337. As long as gate 334 is enabled, the counter counts up. The number of up counts will be proportional to the average absorbance value during the time between $t_{m2}$ and $t_{m4}$, or in other words the value ABS 2 shown on FIG. 3. The down count followed by the up count effectively carries out a substraction of the two counts so that the remaining count in the register will be the difference between ABS 1 and ABS 2. This difference clearly is proportional to the slope of the absorbance signal. Thus, the count stored in register 337 at the time $t_{m4}$ will indicate the rate of change in absorbance, the desired computation. Note that measurement occurs during the full period and is averaged thereover to eliminate errors due to noise. In contrast prior art systems generally measure only at two points to compute slope and are thus subject to large errors due to noise.

Figure 3A:
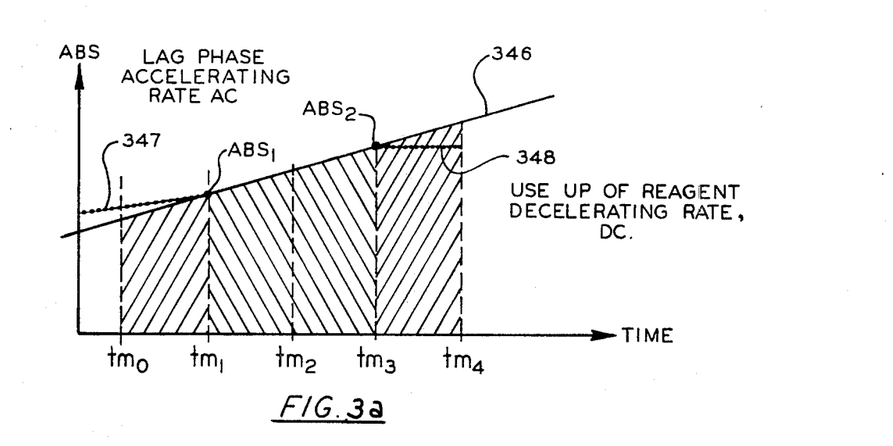

As indicated above, the rate is only valid for kinetic analysis if the curve of the absorbance signal over the measurement period is of a particular linearity. Thus, a curvature check must also be made. The output of divider 332$a$, $b$ or $c$ through switch 331 is also the input to two gates 341 and 343. Again, the outputs of the gates 341 and 343 are inputs to a curvature register 345 comprising a binary up-down counter. FIG. 3a is helpful in understanding the manner in which the curvature determination occurs. Shown is a linear curve portion 346 with dotted lines at the beginning for what is referred to as a lag phase 347 and at the end for what is refer to as use up of reagents 348. The time is broken up into four periods, the first defined by $t_{m0}$ and $t_{m1}$, the second by $t_{m1}$ and $t_{m2}$ the third by $t_{m2}$ and $t_{m3}$ and the fourth by $t_{m3}$ and $t_{m4}$. Times $t_{m0}$ and $t_{m2}$ and $t_{m4}$ are the same times referred to above in connection with FIG. 3.

Flipflops (not shown) similar to flipflops 335 and 336 will be provided to enable gates 341 and 343 to pass pulses from the voltage to frequency converter 323 after being divided and coupled through the switch 331. Gate 341 as indicated, in FIG. 2 will be anabled from the time $t_{m0}$ to $t_{m1}$ and from the time $t_{m3}$ to $t_{m4}$ and the output thereof is coupled into the up input of the curvature register 345. Gate 343 has its output coupled to the down input of curvature register 345 and is enabled from the times $t_{m1}$ to $t_{m2}$ and $t_{m2}$ to $t_{m3}$. Examination of FIG. 3a will show that if the curve is perfectly linear, this will result in a net count of zero. A positive net count will occur for an accelerating rate as would result from the lag phase 347 shown in FIG. 3a, while a negative net count will occur for a decelerating rate as would result from the use up of reagent 348.

After the end of the measurement period as indicated by $t_{m4}$, a command DOCC from the timer indicates that a curvature check should be performed and sets a flipflop 351, as shown in FIG. 2. Flipflop 351 enables a gate 353 which passes an 880 Khz pulse train to the inputs of gates 355 and 357. Each of these gates 355 and 357 have two other inputs which are enabled from the rate register 337. The second input of each gate 355 and 357 is enabled by a condition in rate register 337 indicating none-zero, and the least significant bit output may be used for this purpose. As the third inputs, gate 357 has the positive sign output from the rate sign section of rate register 337, while gate 355 has the negative sign. The output of gate 355 is coupled to the up input of the rate register 337 and that of gate 357 to the down input. These outputs from gates 335 and 357 are also provided to an OR gate 358 having its output coupled as an input to an output register 359 which is a BCD register providing a BCD output to a printer 77. The pulse train output of gate 353 is also divided by 128 in a binary divider 352 from which the output is coupled as an input to gates 361 and 363. These gates 361 and 363 each have two other inputs which are enabled from the curvature register 345. The second input of each gate 361 and 363 is enabled by the zero output of the curvature register 345, which the third inputs thereof are respectively enabled by the positive and negative curvature sign outputs from that register. As shown, the positive and negative curvature indications may be developed by taking the positive sign directly from the register 345 and by obtaining the negative sign through an inverter 373. The output of gate 361 is coupled to the down input of register 345 and the output of gate 363 to the up input. Therefore the pulse train is applied during the curvature check to reduce the accumulated positive or negative count in each register 337 or 345 but to increase the count in output register 359 until the rate register 337 reaches zero. Of course, the gates 355, 357, 361 and 363 will be disabled and the flipflop 351 reset when the rate register 337 reaches zero. If the curvature register 345 reaches before the rate register 337, only the gates 361 and 363 will be disabled causing the curvature register 345 to remain at zero. Otherwise, if after the rate has been loaded into the output register, 359 a count remains in the curvature register 345 the curvature is too great and an indication of this is given because an output remains on line 370 which enables gates 367 and 369 on line 271. Gate 367 has for a second input the positive curvature sign output of register 345 and consequently output therefrom indicates an accelerating rate, while gate 369 has for a second input the output of inverter 373 as the negative curvature sign output of register 345 and consequently output therefrom indicates a decelerating rate. These outputs from gates 367 and 369 are then coupled with the printer 77 to record an error message.

Although the curvature check has been disclosed in connection with the linearly changing rate it is possible through a simple modification to check the curvature on curves which do not change linearly. This may be done in a simple fashion by changing the scale factor within each of the four measuring periods of the curvature determination. Basically two methods of accomplishing this exist. The four periods can be divided up into unequal sections designed to end up with a zero count if the measured curvature follows a predetermined curvature. The other solution comprises keeping constant time intervals and changing the scaling of the count during each of the four quarters. Such scaling may be done in simple fashion by using appropriate divide by N counters similar to divider 352.

Figure 4:
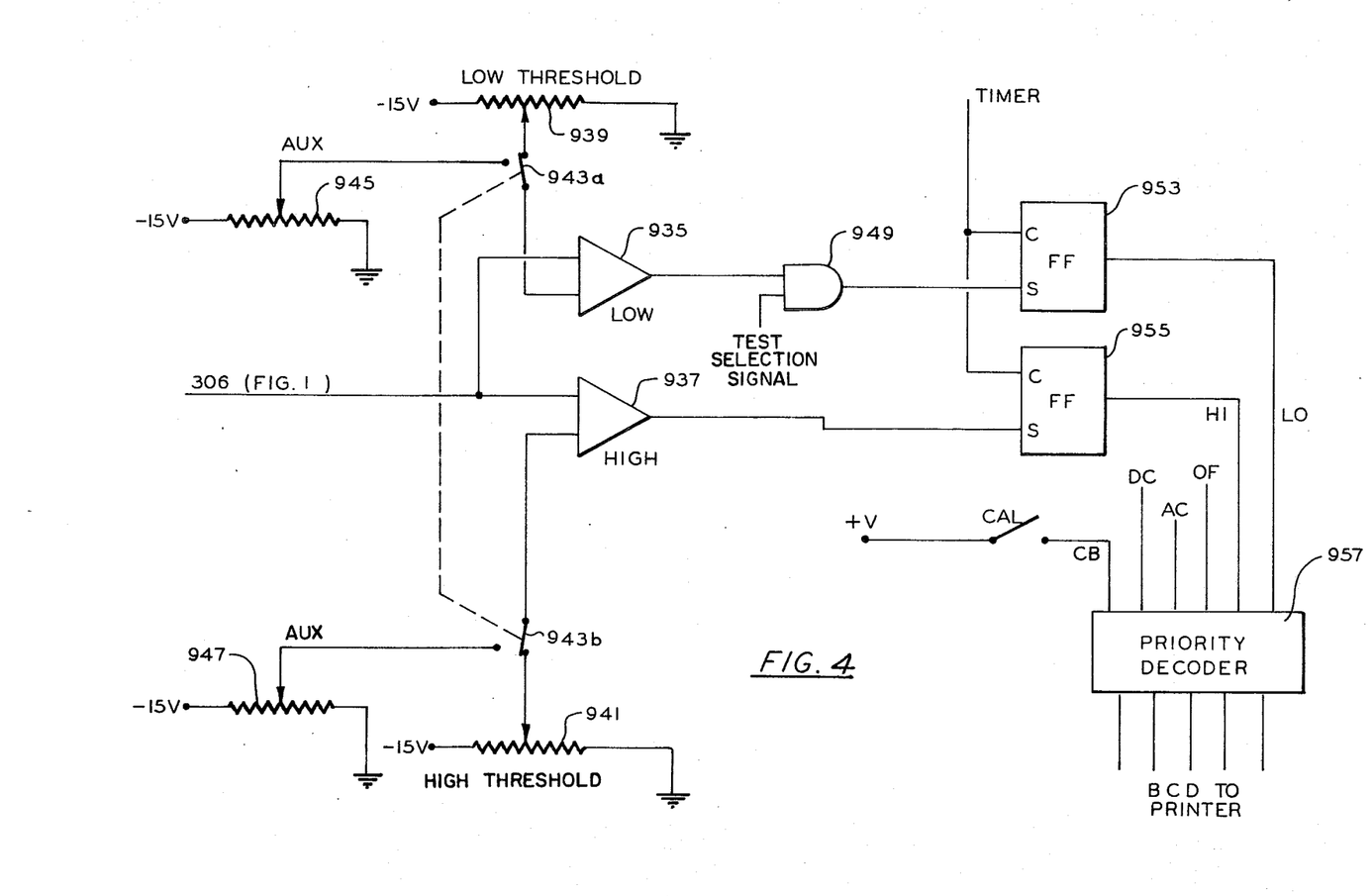
FIG. 4 is a logic diagram illustrating the manner by which upper and lower reaction limits are detected and operation of an error priority decoder within the scope of the present invention.

FIG. 4 shows the high and low absorbance threshold detector along with the error indicating circuitry. Specific high and low thresholds are set in and cover all tests. If these thresholds are exceeded, it is an indication that the desired reaction has not properly taken place and the printed rate is not reliable. The output of the pre-amplifier from FIG. 1 on line 306 is provided to two comparators 935 and 937. The second input of these comparators is respectively the output of either potentiometer 939 or 945 and of either potentiometer 941 or 947 with the selection of the potentiometers being made through a switch having two poles designated 943a and 943b. As with all switches in the apparatus, these will preferably be electronic switches such as FET switches although shown for purposes of simplicity as mechanical switches. All of the potentiometers 939, 941, 945 and 947 are coupled between −15V and ground. When operating from the auxiliary panel, poles 943a and 943b will couple potentiometers 945 and 947 respectively to the threshold comparators 935 and 937. So that the thresholds may be set up by the operator as desired. The output of comparator 935 is provided to an AND gate 949. Which is also enabled by a Test Selection signal indicating that a reaction at a decreasing rate is anticipated. The outputs of gate 949 and comparator 937 are coupled respectively to flipflops 953 and 955 which both receive a clock input from the timer. Of course, flip-flops 953 and 955 only produce outputs when they receive both clock and set inputs. Thus, at the proper time for checking thresholds, a timer output appears at the flipflops and if an error is indicated by 949 or by comparator 937 the appropriate flipflop is set. The output of flipflop 953 thus indicates a low absorbance threshold and that of 955 a high absorbance threshold.

These two threshold inputs along with additional inputs are provided into a priority decoder 957. An overflow indication of is one such input which is received from a flipflop 959 having its set input coupled to the last state (highest count) of the output register 359 of FIG. 2. If this flipflop is set, an overflow situation exists and indication thereof must be given. The next two inputs to the decoder 957 are AC, accelerating rate, and DC, decelerating rate, obtained from the gates 367 and 369 of FIG. 2. The final input is designated CB and is obtained from a switch which is closed when calibration is in progress. The priority decoder 957 may be a Texas Instruments SN74148 and will automatically select the error of highest priority when more than one error is present. The priority of the error signals is listed from left to right on the Priority decoder 957 which provides a BCD output of an error message which is recorded next to the rate obtained from register 359 by the printer 77 in FIG. 2. In addition, presence of an error signal results in the line being printed in red.

Thus, an improved method and apparatus for rate computation has been shown, although specific embodiments have been illustrated and described, it will be obvious to those skilled in the are that various modifications may be made without departing from the spirit of the invention which is intended to be limited solely by the appended claims.

What is claimed is:

1. A method of computing the reaction rate in a sample cell from a signal proportional to absorbance therein, comprising:
    a. integrating the absorbance signal in a first direction for the first half of an observation period to obtain a first value;
    b. integrating the absorbance signal in the opposite direction for the second half of said observation period to obtain a second value; and
    c. differencing said first and second values to obtain a net value proportional to both the average change in the absorbance signal and the reaction rate in the cell over said observation period.

2. The method of claim 1 and further including the step of computing curvature of the reaction rate over said observation period.

3. The method of claim 2 wherein said curvature computing step is accomplished by the steps of:
    a. integrating the absorbance signal in a first direction for the first quarter of said observation period;
    b. integrating the absorbance signal in a first direction for the second and third quarters of said observation period;
    c. integrating the absorbance signal in said first direction for the fourth quarter of said observation period; and
    d. finding the net value of said integrations, said net value being proportional to the curvature of the reaction rate over said observation period.

4. The method of claim 3 and further including the step of comparing said net value proportional to the curvature with said net value proportional to the reaction rate and providing an indication when the former differs from the latter by a predetermined percentage thereof.

5. The method of claim 4 and further including the step of checking the sign of the difference when said predetermined percentage is exceeded and providing a first indication if the difference is positive and a second indication if the difference is negative.

6. The method of claim 5 and further including the steps of changing the scale factor during each quarter of said observation period to verify a non-linear reaction rate.

7. The method of claim 1 and further including the step of converting the absorbance signal to pulses at a frequency proportional thereto and performing said integrating steps by counting said pulses in one direction for the first half of said observation period and in an opposite direction for the second half of said observation period, the net count being inherently proportional to both the average change in the absorbance signal and the reaction rate over said observation period.

8. The method of claim 7 and further including the step of computing curvature of the reaction rate over said observation period.

9. The method of claim 8 wherein said curvature computing step is accomplished by the steps of:
   a. integrating the absorbance signal in a first direction for the first quarter of said observation period;
   b. integrating the absorbance signal in the opposite direction for the second and third quarters of said observation period;
   c. integrating the absorbance signal in said first direction for the fourth quarter of said observation period; and
   d. finding the net value of said integrations, said net value being proportional to the curvature.

10. The method of claim 9 and further including the step of comparing said net value proportional to the curvature with said net value proportional to the reaction rate and providing an indication when the former differs from the latter by a predetermined percentage thereof.

11. The method of claim 10 and further including the step of checking the sign of the difference when said predetermined percentage is exceeded and providing a first indication if the difference is positive and a second indication if the difference is negative.

12. The method of claim 11, wherein said integrating steps of said curvature computing step is accomplished by the steps of:
   a. counting said pulses at the frequency proportional to the
   absorbance signal in a first direction during the first quarter of said observation period;
   b. counting said pulses in the opposite direction during the second and third quarters of said observation period; and
   c. counting said pulses in said first direction during the fourth quarter of said observation period, the net count being proportional to the curvature of the reaction rate over said observation period.

13. The method of claim 12 wherein said step of comparing said net value proportional to the curvature with said net value proportional to the reaction rate and providing an indication when the former differs from the latter by said predetermined precentage is accomplished by concurrently counting the net counts proportional to the curvature and the reaction rate towards zero with the net count of the curvature being counted at a lower frequency than the net count of the reaction rate and providing said indication if the net count of the curvature does not reach zero simultaneously with the net count of the reaction rate, said indication being a first error output when the remaining net count of the curvature is positive and being a second error output when that remaining net count is negative.

14. The method of claim 13 and further including the step of checking the level of said absorbance signal against upper and lower limits and providing third and fourth error outputs respectively if said limits are exceeded.

15. The method of claim 14 and further including the step of printing out decimal representation of the reaction rate along with an additional message that any one of said first, second, third, or fourth error signals is associated therewith.

16. The method of claim 15 and further including the step of assigning a priority to each of said error signals and printing out only the error signal of highest priority.

17. Apparatus for computing the reaction rate in a sample cell from a signal proportional to absorbance therein, comprising:
   a. means for establishing an observation period;
   b. means for integrating the absorbance signal in a first direction during the first half of said observation period;
   c. means for integrating the absorbance signal in the opposite direction during the second half of said observation period; and
   d. means for determining the difference between the two integrations, said difference being proportional to both the average change in the absorbance signal and the reaction rate in the cell over said observation period.

18. Apparatus according to claim 17 and further including means for offsetting the absorbance signal to a value near zero immediately before beginning said observation period.

19. Apparatus according to claim 17 and further including means for computing the curvature of the reaction rate over said observation period.

20. Apparatus according to claim 19 wherein said curvature computing means includes:
   means for integrating the absorbance signal in a first direction during the first quarter of said observation period, means for integrating the absorbance signal in the opposite direction during the second and third quarters of said observation period means for integrating the absorbance signal in said first direction during the fourth quarter of said observation period, and means for determining the net value of said integrations, said net value being proportional to the curvature.

21. Apparatus according to claim 20 and further including means for changing the scale factor during each quarter of said observation period to verify a non-linear reaction rate.

22. Apparatus according to claim 17 and further including means for comparing the absorbance signal level with pre-established maximum and minimum limits and providing first and second error outputs respectively if said limits are exceeded.

23. Apparatus according to claim 17 and further including means for generating pulses at a frequency proportional to the absorbance signal and wherein said means for integrating includes:
   a. an up-down rate register;
   b. means for coupling said pulses to the down input of said rate register during the first half of said observation period; and
   c. means for coupling said pulses to the up input of said register during the second half of said observation period, the net count in said register being proportional to both the average change in the absorbance signal and the reaction rate over said observation period.

24. Apparatus according to claim 23 and further including means for computing the curvature of the reaction rate over said observation period.

25. Apparatus according to claim 24 wherein said curvature computing means includes:
   means for integrating the absorbance signal in a first direction during the first quarter of said observation period, means for integrating the absorbance signal in the opposite direction during the second and third quarters of said observation period, means for integrating said absorbance signal in said first direction during the fourth quarter of said observation period, and means for determining the net value of said integrations, said net value being proportional to the curvature.

26. Apparatus according to claim 25 wherein said integrating means of said curvature computing means includes:
   a. an up-down curvature register;
   b. means for coupling said pulses from said generating means to the up input of said curvature register during the first quarter of said observation period;
   c. means for coupling said pulses to the down input of said curvature register during the second and third quarters; and
   d. means for coupling said pulses to the up input of said curvature register during the fourth quarter, the net count in said curvature register being proportional to the curvature.

27. The apparatus according to claim 26 and further including means for comparing the net count proportional to the curvature with a predetermined percentage of the net count proportional to the reaction rate.

28. Apparatus according to claim 27 wherein said comparing means includes:
   a. an output register;
   b. means for concurrently counting all of said registers, said rate register and said curvature register being counted toward zero and said output register being counted up, said curvature register being counted at a lower frequency than said rate register and said output register being counted at the same frequency as said rate register, said predetermined percentage being proportional to the difference in frequencies of said counting means, said curvature register having a remaining count therein after said rate register reaches zero when the curvature exceeds said predetermined percentage.

29. Apparatus according to claim 28 and further including means for indicating when the curvature exceeds said predetermined percentage.

30. Apparatus according to claim 29 wherein said indicating means includes:
   a. first gate means responsive when said remaining count in said curvature register is positive to provide a first error output; and
   b. second gate means responsive when said remaining count in said curvature register is negative to provide a second error output.

31. Apparatus according to claim 30 and further including means for comparing the absorbance signal level with pre-established maximum and minimum limits and providing third and fourth error outputs respectively when said limits are exceeded.

32. Apparatus according to claim 31 and further including means for sensing overflow conditions from the count in said output register and for providing a fifth error output therefrom.

33. Apparatus according to claim 32 wherein the count of said output register and said error outputs are coupled to a printer.

34. Apparatus according to claim 33 wherein said error outputs are coupled to said printer through means for selecting said error output of highest priority when more than one of said error outputs exist.

* * * * *

UNITED STATES PATENT OFFICE
CERTIFICATE OF CORRECTION

Patent No. 3,963,909  Dated June 15, 1976

Inventor(s) John G. Atwood and Peter H. Heinz

It is certified that error appears in the above-identified patent and that said Letters Patent are hereby corrected as shown below:

Column 1, line 11 ", now abandoned," should be deleted.

Column 3, line 13 "1" should be --/-- and "2" should be deleted.

Column 3, line 23 "what occurs" should be deleted.

Column 3, line 35 --linear-- should be inserted after "is".

Column 3, line 63 insert --is-- after "FIG. 1".

Column 3, line 67 "cycle" should be deleted.

Column 4, line 4 "the" (first occurrence) should be deleted.

Column 6, line 23 "anabled" should be --enabled--.

Column 6, line 50 "335" should be --355--.

UNITED STATES PATENT OFFICE
CERTIFICATE OF CORRECTION

Patent No. 3,963,909          Dated  June 15, 1976

Inventor(s)  John G. Atwood and Peter H. Heinz

It is certified that error appears in the above-identified patent and that said Letters Patent are hereby corrected as shown below:

Column 7, line 8 --zero-- should be inserted after "reaches".

Column 7, line 15 "271" should be --371--.

Column 7, line 59 ". So" should be --so--.

Column 8, line 8, "of" should be --OF--.

Column 8, line 30, "are" should be --art--.

Signed and Sealed this

Twenty-sixth Day of October 1976

[SEAL]

Attest:

RUTH C. MASON
*Attesting Officer*

C. MARSHALL DANN
*Commissioner of Patents and Trademarks*